United States Patent [19]
Jordan et al.

[11] Patent Number: 5,875,282
[45] Date of Patent: Feb. 23, 1999

[54] MEDICAL APPARATUS FOR WARMING PATIENT FLUIDS

[75] Inventors: George Jordan, deceased, late of Fairfield, Conn., by Constance Jordan, legal representative; An Vu, Vista, Calif.

[73] Assignee: Gaymar Industries, Inc., Orchard Park, N.Y.

[21] Appl. No.: 729,645

[22] Filed: Oct. 21, 1996

[51] Int. Cl.$^6$ ....................................................... A61F 7/00
[52] U.S. Cl. ........................ 392/470; 392/485; 219/528; 165/170; 604/114
[58] Field of Search .................................. 392/470, 479, 392/480, 485–489; 219/528; 165/169, 170, 46; 604/114, 113; 137/341

[56] References Cited

U.S. PATENT DOCUMENTS

| | | | |
|---|---|---|---|
| 1,492,821 | 5/1924 | Weinbach . | |
| 3,140,716 | 7/1964 | Harrison et al. . | |
| 3,443,060 | 5/1969 | Smith . | |
| 3,485,245 | 12/1969 | Lahr . | |
| 4,019,020 | 4/1977 | Bilbee et al. | 392/470 |
| 5,073,167 | 12/1991 | Carr et al. | 604/114 |
| 5,245,693 | 9/1993 | Ford et al. | 392/470 |
| 5,381,510 | 1/1995 | Ford et al. | 392/470 |

*Primary Examiner*—Tu Ba Hoang
*Attorney, Agent, or Firm*—Hodgson, Russ, Andrews, Woods & Goodyear, LLP

[57] ABSTRACT

A fluid warming device for warming blood and other fluids prior to introduction into a patient. The counterflow fluid bags utilize a flat counter flow pathway which provides high flow performance and ensuring uniform, gradual and energy efficient blood warming. The warming device contains a pair of opposed, identical heater elements. The guide rails of the bag align the counter flow passageway for the fluid so that the bag is spaced and located precisely between the heater elements. The heater is provided with a receptive slot down the middle, in a horizontal plane, with two different sized guide slots, one on each side of the receptive slot. A pair of guide rails, integrated into the sides of the bag, are parallel to one another providing sufficient rigidity for easy insertion of the bag, and being sized to allow easy insertion in only the correct orientation. The blood warmer preferably incorporates a microprocessor for precise control of the electric current provided to the heater. Fluid temperature is measured by contact of a RTD sensor with a thin dielectric surface layer in contact with the bag and located proximal to the fluid outlet. By monitoring the temperature of the fluid at the outlet of the bag, the temperature controller can compute and provide a visual display of the fluid temperature. In one embodiment, the sensed output temperature is an input parameter to the controller of the heater elements. The device efficiently warms the fluid to about 37.5° C. for anticipated input to a human and, yet, prevents the fluid from exceeding 42° C.

41 Claims, 5 Drawing Sheets

MEDICAL APPARATUS FOR WARMING PATIENT FLUIDS

FIELD OF THE INVENTION

The present invention relates to a medical apparatus for warming blood and other fluids to a desired temperature, prior to introduction of the fluid into a patient.

BACKGROUND OF THE INVENTION AND DESCRIPTION OF THE PRIOR ART

The present invention relates to an apparatus for warming blood and other fluids precisely to a desired temperature, prior to introduction into a patient. Banked blood and blood products are stored under refrigeration and must often be warmed before infusion. Warming is necessary so as to minimize adverse thermal reactions to the patient. Physiologic conditions such as shock, hypothermia, and cardiac disorder can be aggravated by the infusion of fluids even slightly below normal patient body temperature. Thus, a device which precisely and quickly warms stored and refrigerated fluids to body temperature for introduction to a patient is highly desirable.

Fluid warming is typically accomplished with an in-line warming device located between the blood or fluid bag and the patient's venous line. Heating occurs as the fluid passes through a heat exchanger within the warming device. Conventionally, the heat exchanger uses a disposable insert intended for single patient use only. Because the warming device is primarily used to warm blood it is often referred to as a blood warmer, yet the device is also suitable for warming IV solutions and other blood-related products intended for introduction into the patient.

There are many blood-related products available to the clinician for transfusion therapy. Whole blood, packed red cells, fresh frozen plasma and platelet concentrates are among the more commonly used products. The present invention is suitable for warming all of these fluids, as well as blood and IV solutions, too.

The American Association of Blood Banks (AABB) has set standards for the storage of blood-related products. A temperature of between about 1° to 6° C. is required. The AABB further recommends warming before infusion of the products into the patient and advises that the warmed blood-based products should not exceed 42° C. Warming above this upper limit can cause irreparable damage to the red blood cells, including hemolysis, and possible harm to the patient.

As medical science has advanced, the demands for infusion of body fluids, particularly whole blood, have grown. Today, infusion rates range from one to two units of whole blood infused over a two hour period for a typical adult having undergone coronary surgery, to over a unit per minute in the case of a multiple wound gunshot victim being treated in a trauma center. The flow rates involved range from about 10 cc/min to 500 cc/min.

Whole blood is conventionally stored in 500 cc bags. Each such blood bag is referred to as a unit. The bags are hung on a pole above the blood warmer and above the patient. Gravity causes flow of the blood from the bag, through the warmer, and into the patient. To meet the demands of high blood infusion rates the bags are often placed inside pressure infusers that force the blood out of the bag at a higher flow rate than gravity alone can provide.

Since normal human body temperature is 37.5° C., physicians desirably would like to warm all fluids to human body temperature prior to patient introduction. This is believed to provide optimal patient care and minimal thermal "shock" due to blood or fluid infusion. The goal of the blood warmer device is to rapidly warm fluids from the lowest storage temperature of 1° C. to the desired patient introduction temperature of 37.5° C., without any overheating, at all flow rates between about 10 to 300 cc/min, and to accommodate rapid changes in flow rates, all without over or under heating of the blood or fluid.

The challenge of wide dynamic temperature and fluid flow rates and the fact that the maximum allowable temperature (42° C. per AABB) is close to the final desired output temperature (37.5° C.) places high expectations and demands on the construction and operation of an effective blood warmer.

In U.S. Pat. No. 3,443,060, a plastic bag carrying blood for a patient is maintained at a thermostatically controlled temperature. The device employs a cylindrical heated mandrel around which a flat plastic bag is telescoped and an outer hollow cylindrical mandrel also telescoped over the bag and the inner mandrel. Longitudinal ribs formed on one of the mandrels press the bag walls together under the ribs to form a labyrinth of passageways through the bag. Inlet and outlet connections for conducting the blood supply to the bag and from the bag to the patient are provided. There is no teaching in the '060 patent for providing a sensor for the fluid within the bag, nor is there a teaching of a counter flow pathway for uniform heating of the fluid, nor any mention of a back-up system to prevent any over heating of the blood.

U.S. Pat. No. 4,019,020 relates to a controlled temperature fluid heater. The device is intended to maintain the fluid supply at optimum temperature for infusion into a patient by employing a flat plastic bag having a labyrinth of inner flow passageways. There is no teaching or suggestion of providing a sensor for the fluid within the bag, nor any teaching of a counter flow pathway for uniform heating of the fluid, nor any mention of a back-up system to prevent any overheating of the blood.

U.S. Pat. No. 3,485,245 shows a portable heater for heating fluids to the correct body temperature prior to intravenous injection. The fluid is directed in a serpentine-like path through a disposable, heat conductive pouch. The pouch is held between heating platens. Temperature sensors are located in the heating unit and an automatic control seeks to ensure that fluid is delivered at the correct temperature. This reference does not teach the use of a counter flow pathway to uniformly heat the fluid nor does it include any teaching of safety system(s) to prevent overheating of the blood.

U.S. Pat. No. 1,492,821 relates to an antifreezing device. Basically, the device is used to prevent water pipes, especially those in automobiles, from freezing. The device comprises a hinged box for surrounding the pipe. A heating electric coil, arranged in a zig zag pattern, is located within the box and, when power is supplied, heats the pipe. Clearly, this '821 patent neither teaches nor suggests the subject invention relating to rapid blood warming for patients.

U.S. Pat. No. 5,073,167 teaches a device which heats blood with microwaves. This method of energy transfer in itself makes for a drastically different piece of equipment. In contrast, the present inventors' method of over temperature protection depends on the gradual increase of a large mass transferring energy to the heat exchanger and the monitoring of the temperature of that large mass.

U.S. Pat. Nos. 5,245,693 & 5,381,510 show heaters for heating fluids prior to intravenous injection through a special cassette of rigid plastic and thin metal layers. The fluid is pressure regulated through a serpentine pathway in the disposable cassette. The cassette is held between two heating zones with multiple temperature sensors and an automatic control seeks to ensure that fluid is delivered at the set temperature. This preference does not teach the use of a counter flow pathway to uniformly heat the fluid nor does it rely on an energy reservoir.

Several disadvantages have been observed in prior art blood warmers, namely:

a) Overheating of the red blood cells, i.e. heating beyond the maximum allowable temperature. This can happen when, for example, little fluid is left in a blood bag and the flow rate is low;

b) Rupture of blood cells due to mechanical trauma;

c) Inadequate heating of the blood to the desired, optimal patient introduction temperature;

d) Uneven heating of the blood when increased flow rates are demanded; and, e) Expensive single patient-use components.

Blood warming prior to patient infusion dates back to around 1941. Early blood warmers consisted of containers of warm water that the bags of blood were placed into for a period of time prior to infusion. This is similar to the procedure of heating frozen vegetables, contained in a plastic pouch, by immersing the same in heated water. A few decades later, more sophisticated water bath blood warmers, like the Dupaco Hemokinetherm and American McGaw N3001, were introduced. They used electrical heater elements to maintain a reservoir of water at substantially 37° C. while the blood flowed through a disposable coil of tubing, immersed in the heated water.

A recent application of the water bath principle for blood warming is found in the Level 1 Technologies device, marketed as a Fluid Warmer. In this device, water is maintained at a fixed temperature near 42° C. and pumped through a "counter current" heat exchanger tube. The disposable heat exchanger tube uses a double lumen, aluminum tube to allow blood to flow in one direction and water to flow in the other. The energy is transferred from the water through the aluminum sidewall to the blood, to warm the blood. The counter current flow gives this technology a higher warming capacity than the earlier water bath types but the disposable heat exchanger tube is rather expensive. The system seems bulky and messy to operate. The present invention uses electric heater elements. This eliminates the mess and other disadvantages associated with water heater-type fluid warmers.

The DATACHEM FloTem II dry heat fluid warmer uses large metal plates, heated with an electric heater, to raise the temperature of stored fluid prior to introduction into the patient. A length of tubing is laid next to the hot plates and fluid flowing through the tubing is heated via conduction. The system does not employ microprocessor temperature controls. In contrast, the present invention has a design wherein the actual temperature of the outlet fluid is monitored for precise control of the fluid temperature. The prior art device does not measure or display fluid temperature, only warming plate temperature.

Fenwal Laboratories' BW-5 is another example of a dry heat fluid and blood warmer. Like the DATACHEM device, the BW-5 unit also heats aluminum plates with electric heater elements. Plates are maintained at a desired temperature by a simple control circuit, again based on plate temperature. This unit incorporates a bag rather than heat conductive tubing as the mechanism for energy transfer. The BW-5 seeks to measure blood temperature by the use of a thermistor in the aluminum plate near the exit port of the heat exchanger bag. This thermistor is used to display blood temperature, but no control of the heater elements as a function of the sensed fluid temperature is accomplished or taught by the BW-5.

In contrast, the present invention uses the sensed fluid temperature to actually control the power provided to the heaters. The manner in which the blood temperature measurement is taken in the BW-5 device is such that a high degree of error can be expected and the measurement was thus not thought suitable for heat control purposes. A portion of this measurement error was attributable to the lack of precise registry and alignment between the bag and the temperature sensors. No mechanism for ensuring registry or alignment was provided. The present invention employs a pair of parallel guide rails secured to the sides of the disposable bag. The rails slide into and are received by spaced slots in the warming device. These rails are color coded and are of different sizes to prevent the user from inserting the bag incorrectly. Without these features, the temperature measurement of the fluid is not suitable for feedback to provide precise electrical/heating control. Another difference between the BW-5 and the present invention is that the BW-5 has a single heater whereas the present invention has two heaters. This results in more controllable and uniform heating.

Another device, the Animec AM-4 (made in Japan) is almost identical in design to the BW-5. It also incorporates a bag type heat exchanger and an output temperature sensor. No use is made of the output temperature for electrical power/heating control because of the same limitations on measurement accuracy believed to be found in the BW-5.

Yet another prior art dry warmer is American Medical Systems' DW1000D. Like the others, this device incorporates a solid aluminum heater and measures and displays only heater temperature. The heater in that device is cylindrical. The heat transfer bag is wrapped around the heater and is held in place by a curved plexiglass cover. While interesting in that the cover lets the operator view the fluid as it flows through the warmer, having a heater element contact only one side of the heat exchanger bag dramatically reduces the heating capacity and uniformity of fluid heating. A major disadvantage of all the "dry warmers" is that the installation of the disposable heat exchanger bag takes more time and is more difficult. Also, the extra moving parts could cause leaks in the disposables and provide for more failure modes in and of themselves. The present invention is believed far more efficient and accomplishes its task in a far more accurate and uniform manner.

Neither the DW1000D nor any of the other prior devices teach the use of slots on the warmer device and corresponding guide rails on the fluid bag which cooperate for aligning and registering the heat transfer bag into the warmer. The DW1000D has a plexiglass cover that opens up. The FloTem II and BW-5 incorporate a metal door that is opened to install the bag. Without the use of the guide rails incorporated in the present invention, a bag does not have enough rigidity to be inserted into a slot without "bunching up". With the guide rails, installation is quick and easy. The guide rails also facilitate accurate temperature measurement of the fluid and ensures more efficient and uniform heating. The guide rails ensure proper alignment of fluid input and output with the warmer.

SUMMARY OF THE INVENTION

The present invention overcomes many of the shortcomings found with the prior art devices. The counterflow bags of the present invention utilize a flat counter flow pathway which provides high flow performance and yields more uniform fluid heating. The blood warmer described and disclosed herein incorporates a microprocessor for precise control of the electric current provided to the heater. Energy transfer is accomplished by conduction, convection and radiation from heater plates, on both sides, to the disposable bag. The fluid warmer system consists of a reusable heater/controller and a single patient use fluid bag that serves as the disposable component of the heat exchanger.

The present invention basically comprises a small appliance-sized heater, similar in size to a laptop computer. The heater is provided with a receptive slot down the middle, in a horizontal plane, with two different sized guide slots, one on each side of the receptive slot. A pair of guide rails, integrated into the sides of the bag, are parallel to one another. They provide sufficient rigidity for easy insertion of the bag. The guide slots and the rails of the bag are sized to allow easy insertion in only the correct orientation. The disposable bag is provided with inlet and outlet lines secured to the bag. When the bag is inserted into the warmer, the inlet and outlet lines are supported by rounded cutouts in the heating element. The bag has selected portions heat sealed together so that the blood/fluid is forced to travel in a counter flow path, the coldest fluid starting at the inlet line, and flowing through the path to exit as the warmest fluid through the outlet line. The counterflow path ensures uniform, gradual and energy efficient blood warming. The device is ready to use within one minute of turning on the power.

The warming device contains a pair of opposed, identical heater elements. One is located on each side of the slot for the bag. The guide rails of the bag align the counter flow passageway for the fluid so that the bag is spaced and located precisely between the heater elements. The amount of electrical power delivered to the heaters is controlled by a microprocessor-based temperature controller. The fluid temperature is measured by contact of a RTD sensor with a thin dielectric surface layer in contact with the bag. The temperature sensor is located proximal to the fluid outlet. By monitoring the temperature of the fluid at the outlet of the bag, the temperature controller can compute and provide a visual display of the fluid temperature. In one embodiment, the sensed output temperature is an input parameter to the controller of the heater elements.

It is another important aspect of the present invention to provide a fluid warming device which efficiently warms the fluid to about 37.5° C. for anticipated input to a human and, yet, preventing the fluid from exceeding 42° C. It is another specific aspect and advantage of the present invention to provide a user-friendly blood/fluid warming device able to fit and be supported horizontally on an IV pole or under some operating tables, or even vertically, in a manufacturer supplied bracket.

The safety of the present invention is ensured by the next special feature, the over temperature prevention system. The temperature controller has a programmable alarm feature which causes an audible alarm when the fluid temperature rises above 42.1° C. In the event of controller malfunction or an internal electrical short, there are two temperature sensing switches located in the heater element designed to terminate the power to the heater elements or to the whole unit as the situation requires.

These and other objects are solved by the present invention. The invention will be understood more fully, while still further objects and advantages will become apparent, in connection with the following detailed description of a preferred embodiment thereof, illustrated in the accompanying drawings.

DETAILED DESCRIPTION OF THE DRAWINGS AND THE PREFERRED EMBODIMENT

Figure 1:
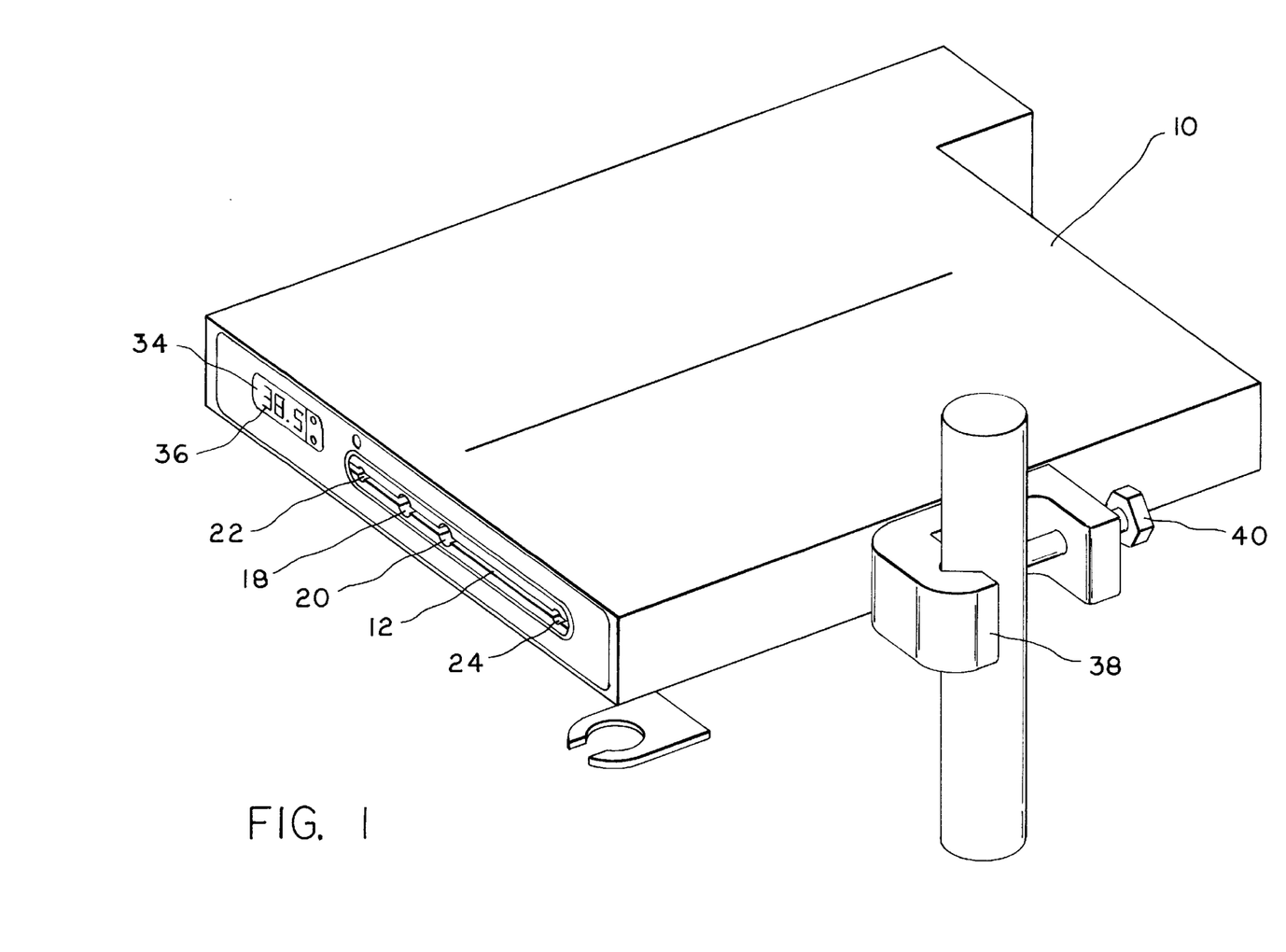
FIG. 1 is a perspective view of the blood or fluid warming device of the present invention, supported horizontally on an IV pole, only partially shown.
Figure 2:
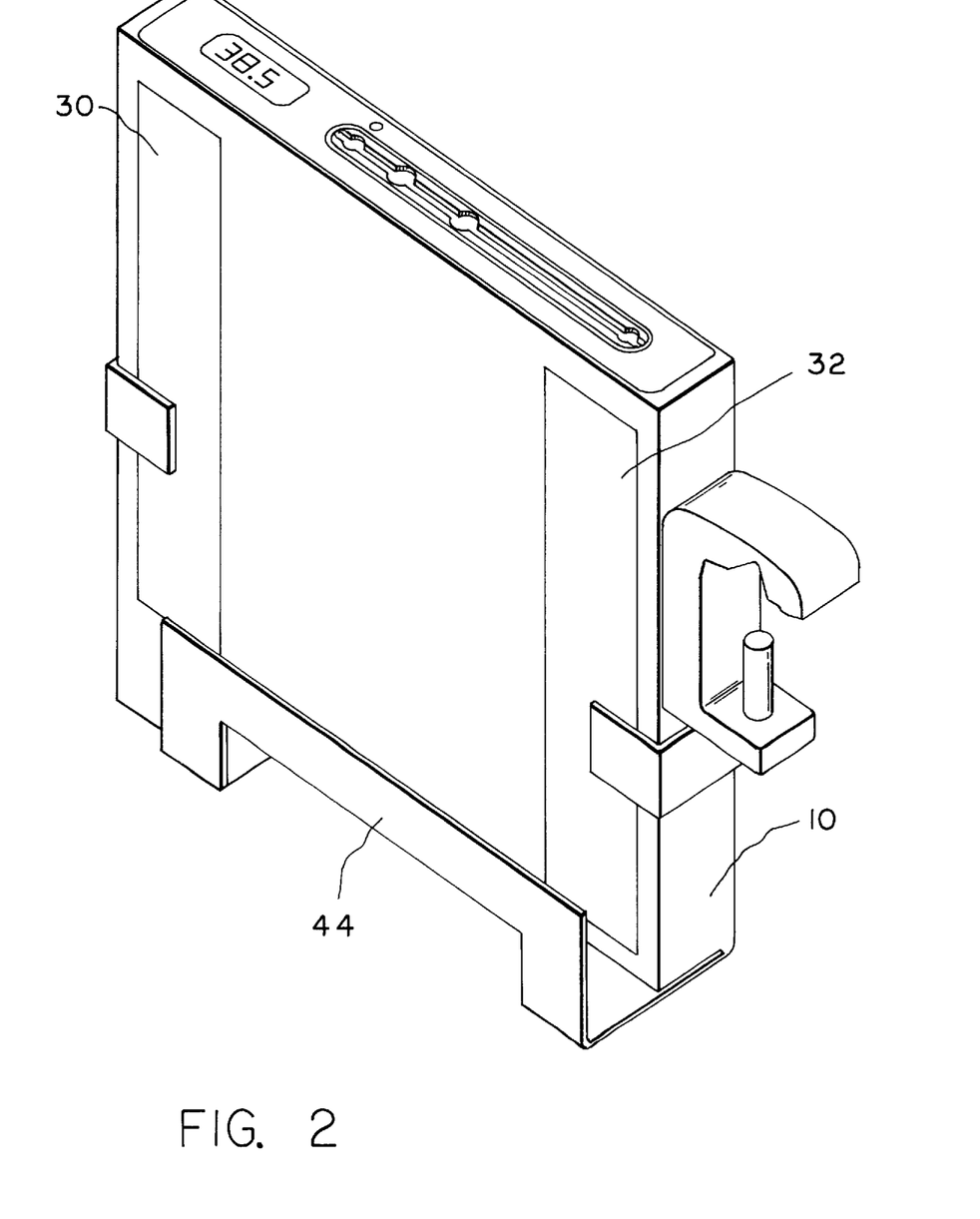
FIG. 2 is a perspective view of the present invention shown in FIG. 1, held with its bag-receiving slot extending vertically.
Figure 3:
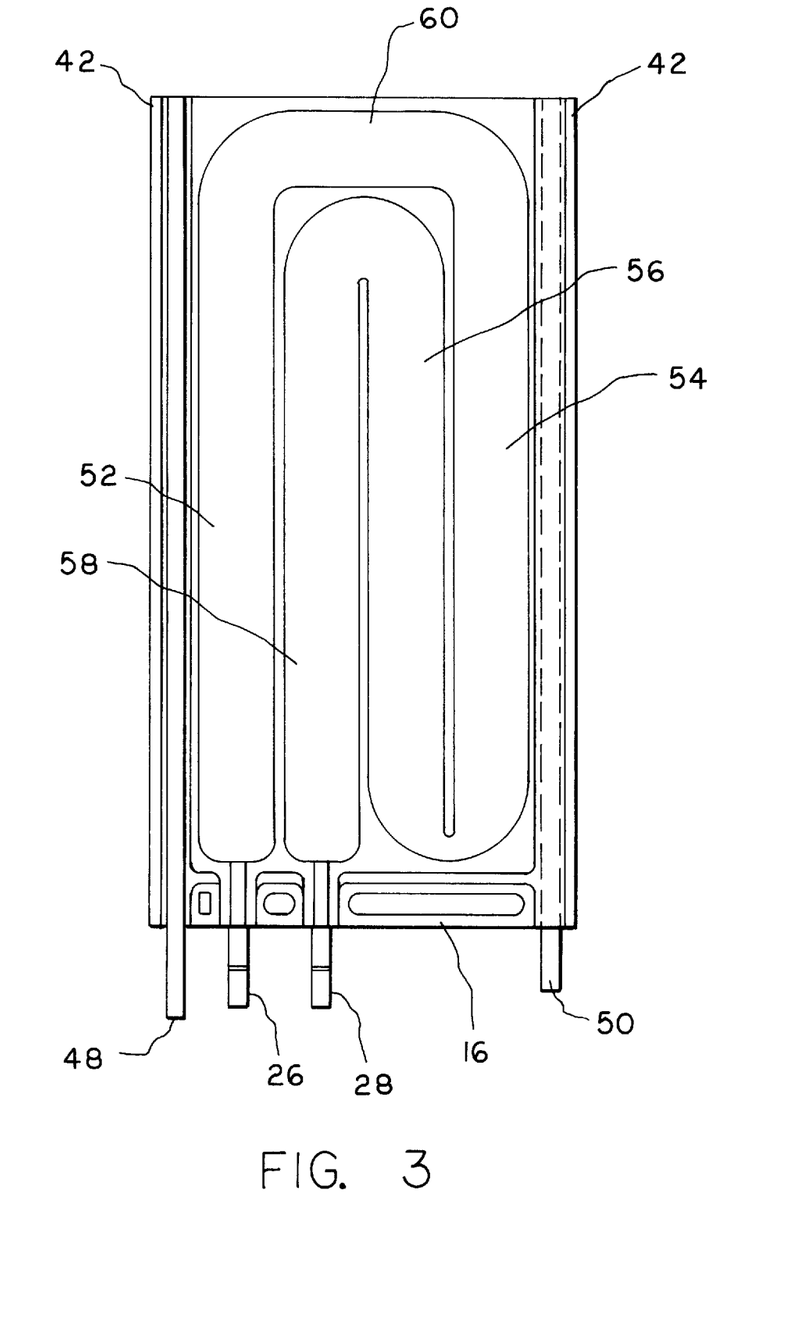
FIG. 3 is a top plan view of the blood or fluid warming bag intended for use with the device of FIGS. 1 and 2.

As shown in FIG. 1, a warmer controller device 10 houses the electrical heating elements. The single frame instrument has a longitudinal extending slot 12 on the front 14 of the warmer capable of receiving the heat exchanger bag 16 (FIG. 3). The bag 16 and warmer 10 cooperate to provide a parenteral fluid warming system. The slot 12 of the warmer 10 has integrated openings 18, 20, 22, and 24 for accommodating tubular inlet 26, tubular outlet 28, blue large guide rail 48, and white, relative natural small guide rail 50, respectively (FIG. 3). The front face of the warmer 10 is provided with a visual display 34 for showing, by digital readout, the temperature of the fluid near the outlet 28 in degrees Celsius. For illustrative purposes, the illustrated device has a digital temperature indicator 36. The device can be mounted on an IV pole in a horizontal position by adjusting the knob 40 of clamp 38. Also, it can be placed in the x-ray table slot of the O.R. In addition, the device may be provided with slip resistant foam 30 and 32. For a third alternative, the device can be vertically oriented on an IV pole, or with a 15° angle, by placing the warmer 10 into a bracket 44 (FIG. 2).

FIG. 3 shows a plan view of the heat exchanger blood/fluid warming bag 16. Tubular openings 42, located at outer edges of the bag, sealingly contain the guide rails 48 and 50. The rails are made from rigid plastic. They provide structure/rigidity, and support the heat exchanger bag 16. Rails 48 and 50 are color coded and may be of different diameters cross-sectional or shapes to engage and mate with guide channels or slots, 22 and 24 respectively, located in warmer 10. The guide channels 22 and 24 are parallel to one another to ensure smooth insertion of the bag or heat exchanger 16. These guide channels allow easy insertion of the bag or heat exchanger 16 and guide tubular inlet 26 and tubular outlet 28 help maintain precise registration and alignment of the bag with respect to the heater elements contained within device 10. The rails 48 and 50 also ensure that the bag is stretched across the planar heater elements and also ensure the bag or heat exchanger 16 physically contacts or is close to the temperature sensor at the fluid outlet 28 to facilitate uniform heating. The heat exchanger (blood/fluid warming) bag is constructed of four thousandth of an inch (0.004") thick polyethylene. Heat sealing techniques familiar to those skilled in the art are used for construction of the bag in accordance with the present invention. For example, the inlet, outlet the guide rails and the serpentine fluid flow path between inlet and outlet, can all be formed, using heat sealing of the bag.

FIG. 3 shows the heat seal pattern used in the manufacture of the preferred embodiment of the bag. The fluid path is depicted in FIG. 3 to have five sections, four parallel portions (52, 54, 56 & 58) to each other and one perpendicular segment (60). The fluid inlet 26, which is open to the fluid path 52, allows cold flow fluid into 52 then to segment 60, onto portions 54, 56 and then to 58 which is open to outlet 28. Each fluid pathway is equal in width. Fluid pathway inlet portion 52 is adjacent to fluid pathway outlet portion 58 to facilitate uniform heat distribution for all areas by setting up a thermal counter balance.

Figure 4:
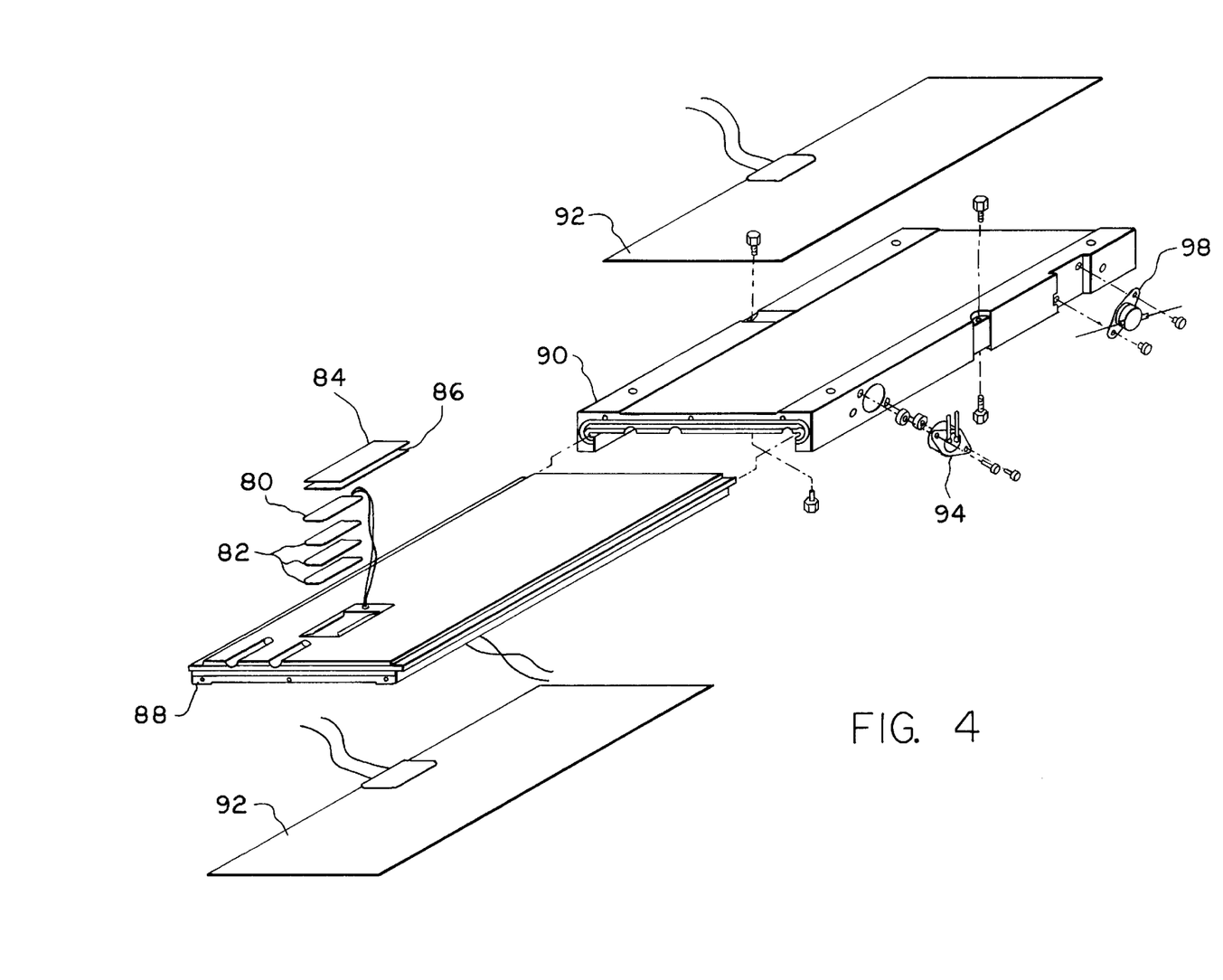
FIG. 4 is an exploded view of the internal components of the blood/fluid heater shown in FIGS. 1 and 2.

FIG. 4 shows an exploded view of the energy reservoir 88 and 90. There are two identical heater pads 92 vulcanized to energy reservoirs 88 and 90 contained in the device 10. One is located on each side of slot 12. As the bag or heat exchanger 16 is inserted into slot 12 it precisely aligns the outlet flow path portion with sensor 80. The alignment and registry between the guide rails 48 and 50 of the heat exchanger 16 and mating guide channels 22 and 24 of the device 10 guarantees that this results.

Each heater element 92 is silicone rubber and vulcanized to the energy reservoir 88 and 90. The general principles of construction are believed standard to the industry. The heater element 92 is a thin film, insulated by thirty-two hundredths of an inch (0.032") thickness of silicone rubber having the capacity to produce 500 Watts at 120 VAC input. Suitable heater elements are well known and available in the art. (For example, suitable heater elements are manufactured by Watlow Inc. of Saint Louis, Mo.)

Sensor 80 is a resistance temperature detector (RTD) type PT 100 located near fluid path outlet 28 of the heat exchanger. Sensor 80 is thermally insulated from the energy reservoir 88 and 90 by three layers 82 of Teflon®. The RTD sensor 80 is covered by a layer of high temperature adhesive 86 and a thin layer of stainless steel 84. Total distance from sensor 80 to the fluid in the heat exchanger is ten thousandths of an inch (0.010"). Suitable sensors are well known and available in the art. (For example, a suitable sensor is manufactured by Minco Products Inc., of Minneapolis, Minn.)

Referring to FIG. 3, the cold flow of fluid enters the heat exchanger 16 at inlet port 26, flows through flow path portion 52 to the left side of heat exchanger 16 through the bottom segment 60, then through right side (farthest side) fluid path portion 54, continues to fluid path portion 56 with a 180° turn from fluid path 54, and then continues to outlet fluid path portion (58) with another 180° turn from fluid path 56. Fluid path 58 is the warmest fluid path portion and is located in the middle of the coldest path portion 52 and a colder path portion 56, causing a thermal counter balance of energy. The RTD sensor is located near outlet 28 where fluid exits the heat exchanger 16. The automatic temperature controller stabilizes at a preset temperature limit causing a thermal counter balance with the energy reservoir.

The described sensor in its specific location is the key to the control system. The thermal feedback system used is a proportional, integral, derivative (PID) temperature controller. This is a control mode with three functions. The "proportional action" dampens the system response. "Integral" corrects for droop. "Derivative" seeks to prevent overshoot and undershoot. The sensor input sampling rate is 10 samples/second of the fluid exiting the heat exchanger 16. A thermal counterbalance of fluid exists from the heat exchanger 16 compared to a predetermined set temperature which is the feedback signal to PID temperature controller 100. The temperature controller will adjust and replenish any energy lost to the energy reservoir 88 and 90 through the heater elements 92.

The primary PID temperature controller maintains a temperature of approximately 35° to 40° C. in the fluid over the flow range of 10 to 300 ml/min for 10° C. fluid input. For 20° C. or above, the fluid input may be warmed to a flow rate of 500 ml/min. If the primary controller senses a fluid temperature above 42° C. an audible alarm will also sound and cut off power to the energy reservoir. The unit will await a fluid temperature drop below 42° C. before turning off the audible alarm.

When the primary controller senses a fluid temperature below 34° C. an audible alarm will also sound and automatically adjust power to the energy reservoir, awaiting fluid temperature rise above 34° C. before turning off the audible alarm.

The temperature controller is recognized to be regularly available in the art. (The PID primary temperature controller 100 is preferably a series 935 auto tuning controller manufactured by Watlow Control of Winona, Minn.).

If the energy reservoir temperature reaches a predetermined temperature, an audible alarm will sound and power will cut off to the energy reservoir and PID controller. The audible alarm can only be terminated by removing the power cord from the wall socket. The safety cut-out switch 94 is well known and available in the art. (An example of a suitable back up mechanical temperature switch 94 is the Hermetic thermostat series 3100U, manufactured by Elwood Sensors, Inc. of Pawtucket, R.I.).

Figure 5:
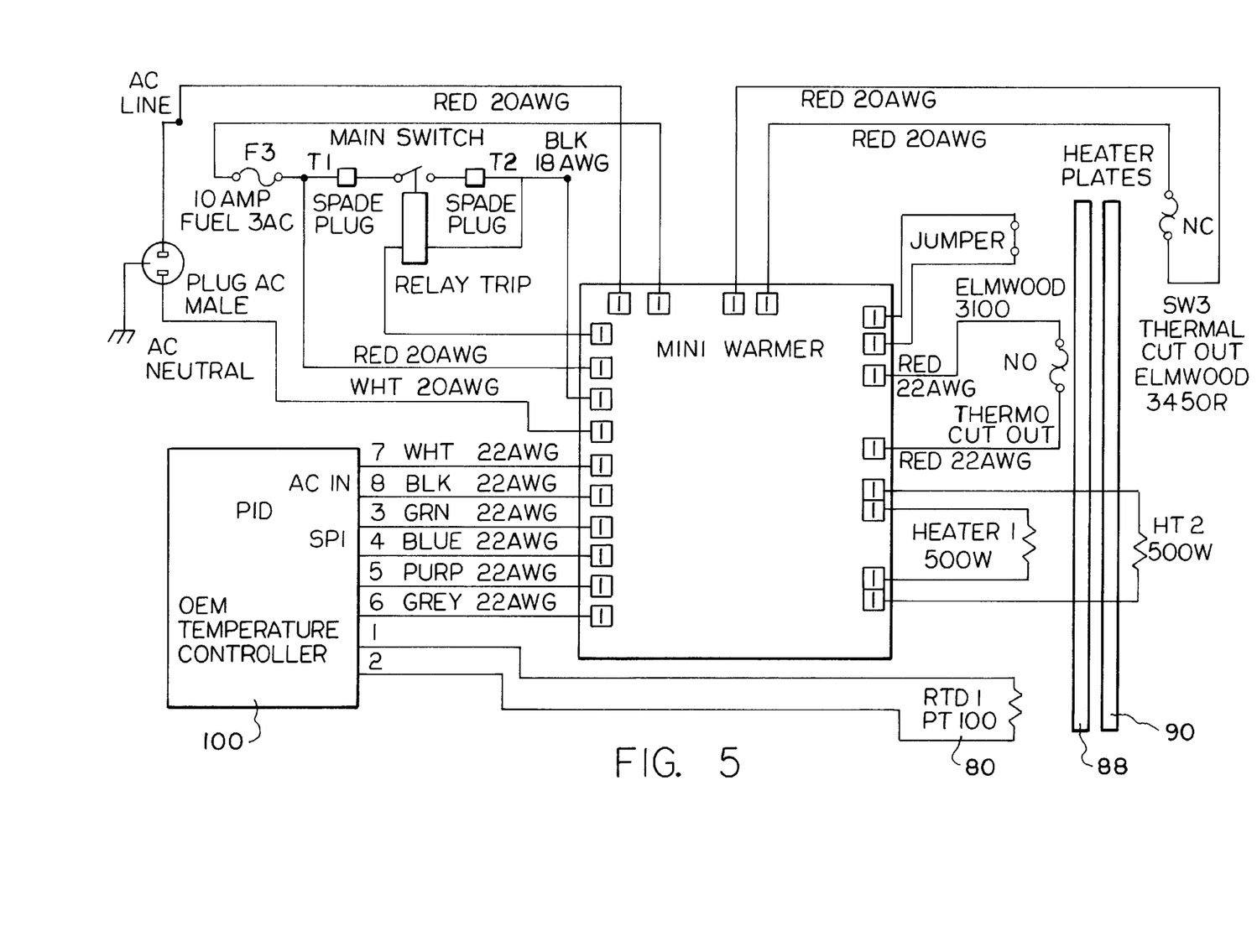
FIG. 5 is an electrical schematic and block diagram of the blood/fluid warming device of FIGS. 1 and 2.

As shown in the circuit diagram in FIG. 5, if there is a catastrophic failure, and the temperature of the energy reservoir rises to 45° C., a safety cutout bimetallic switch which is embedded in the energy reservoir cuts off all power to device 10. No audible alarm is heard and the temperature display 36 goes blank. Suitable bimetallic switches are well known and available in the art. (A suitable bimetallic switch, for example, is Model 3450R manufactured by Elmwood Sensors, Inc. of Pawtucket, R.I.).

Consequently, the four component, temperature sensing and electrical signal control system preferably comprises:

a) A Proportional, Integral, Derivative temperature controller, 1/32 DIN;

b) Primary Temperature Control Sensor Resistor Temperature Detector, PT-100;

c) A Back Up Temperature cutoff, hermetic thermostatic independent cutoff power PID and energy reservoir; and, d) A thermal cutout bimetallic switch which will independently cut off power to device 10.

Thus, to allow maximum user flexibility, especially important in emergency hospital care, a blood/fluid warming system is designed and provided in which the heat exchanger 16 is easily inserted into slot 12 of warmer device 10. For proper operation, the heat exchanger bag 16 must be completely inserted into slot 12 of device 10 by aligning guide rails 48 and 50 of heat exchanger 16 with mating slots 22 and 24, respectively, of device 10. The bag or heat exchanger is continued to be inserted to the stop position where rail 50 is completely inside slot 24 to ensure it is in place.

Having described the invention with regard to certain specific embodiments thereof, it is to be understood that this description is not meant as a limitation since further modifications may now suggest themselves to those skilled in the art, and it is intended to cover such modifications as fall within the scope of the appended claims.

We claim as follows:
1. A parenteral fluid warming system comprising:
   a) a fluid warming bag having an inlet, an outlet, and a counter flow fluid path extending between said inlet and said outlet, said counter flow fluid path being a serpentine path having its coldest fluid path portion positioned adjacent to its warmest fluid path portion, wherein said coldest fluid path portion is the portion of said fluid path receiving fluid from said inlet, and said warmest fluid path portion is the portion of said fluid path providing fluid to said outlet, and said bag having alignment means in the form of parallel guide rails; and
   b) a warmer evice, having one energy reservoir with at least one heater, said bag being capable of being placed in thermal proximity to said energy reservoir such that said heater warms fluid passing through said fluid path.
2. A parenteral fluid warming system as claimed in claim 1 wherein said warmer device comprises two heaters, said fluid warming bag being located between said heaters.
3. A parenteral warming system as claimed in claim 1 wherein said warmer device is provided with cooperating registry means such that said bag, when inserted into said warmer device, precisely aligns and registers said fluid path.
4. A parenteral fluid warming system as claimed in claim 3 wherein said fluid warming bag has outside edges, and said alignment means comprises at least two guide rails secured to said outside edges of said fluid warming bag, said guide rails being different sized to prevent misinsertion.
5. A parenteral fluid warming system comprising:
   a) a fluid-warming bag having an inlet, and outlet, and a counter flow fluid path extending between said inlet and said outlet, said counter flow fluid path being a serpentine path having its coldest fluid path portion positioned adjacent to its warmest fluid path portion, wherein said coldest fluid path portion is the portion of said fluid path receiving fluid from said inlet, and said warmest fluid path portion is the portion os said fluid path providing fluid to said outlet; and
   b) a warmer device, having one energy reservoir with at least one heater, said bag being capable of being placed in thermal proximity to said energy reservoir such that said heater warms fluid passing through said fluid path; and
   c) said fluid warming bag is provided with alignment means and said warmer device is provided with cooperating registry means such that said bag, when inserted into said warmer device, precisely aligns and registers said fluid path; and
   d) wherein said alignment means are color coded.
6. A parenteral fluid warming system as claimed in claim 3 wherein said registry means comprises at least two slots for receipt of said alignment means.
7. A parenteral fluid warming system as claimed in claim 4 wherein said guide rails are a parallel pair located along said outside edges of said fluid-warming bag and said registry means comprise a pair of slots located in said warmer device, said slots being capable of mating receipt of said guide rails.
8. A parenteral fluid warming system as claimed in claim 2 wherein said warmer device is provided with fluid temperature sensing means near said outlet.
9. A parenteral fluid warming system as claimed in claim 1 wherein said warmer device is provided with fluid temperature sensing means to detect the temperature of the fluid contained within said fluid-warming bag.
10. A parenteral fluid warming system as claimed in claim 9 wherein said fluid temperature sensing means is provided proximal to said fluid-warming bag.
11. A parenteral fluid warming system as claimed in claim 1 wherein said warmer device is provided with energy diffusing means to ensure that the energy generated by said at least one heater is uniformly distributed.
12. A parenteral fluid warming system as claimed in claim 8 wherein said warmer device is further provided with display means capable of indicating the temperature of said fluid at said outlet.
13. A parenteral fluid warming system as claimed in claim 1 wherein said energy reservoir is provided with maximum temperature shut-off means to ensure that no power is provided to said at least one heater when a predetermined maximum temperature is reached at said energy reservoir.
14. A parenteral fluid warming system as claimed in claim 10 wherein said fluid temperature sensing means are substantially thermally insulated from sensing the temperature of said energy reservoir.
15. A parenteral fluid warming system as claimed in claim 14, further comprising thermal insulation interposed between said fluid temperature sensing means and said energy reservoir, said thermal insulation comprising two hundredths of an inch (0.020) of spacing.
16. A parenteral fluid warming system as claimed in claim 8 wherein said temperature sensing means are located about a plane parallel to said energy reservoir.
17. A parenteral fluid warming system as claimed in claim 9 wherein said fluid temperature sensing means are located about a plane parallel to said energy reservoir.
18. A parenteral fluid warming system as claimed in claim 13 wherein said maximum temperature shutoff means is located on the plane perpendicular to said energy reservoirs.
19. A parenteral fluid warming system as claimed in claim 1 wherein a pair of said heaters are provided, said heaters being opposed to one another, with said fluid warming bag being located between said heaters.
20. A parenteral fluid warming system as claimed in claim 8 wherein the power provided to said heaters is determined as a function of the temperature sensed by said temperature sensing means.
21. A parenteral fluid warming system as claimed in claim 9 wherein said fluid temperature sensing means is ten thousandths of an inch (0.010") from said fluid.
22. A parenteral fluid warming system as claimed in claim 1 wherein said energy reservoir is controlled by a microprocessor-based system controller, which controls the temperature of said energy reservoir based on temperature data of the fluid passing through the outlet of said fluid warming bag.
23. A parenteral fluid warming system as claimed in claim 22 wherein said system controller adjusts the power to said heaters; measures and provides a display of the temperature of said fluid at said outlet, and is further provided with a maximum temperature shutoff means.
24. A parenteral fluid warming system as claimed in claim 1, wherein electrical power to said at least one heater is shut off if the temperature sensed exceeds a perdetermined maximum.
25. A parenteral fluid warming system as claimed in claim 1 wherein the device is provided with means for attachment to an IV pole for use in the horizontal position.
26. A parenteral fluid warming system as claimed in claim 1 wherein said device is water resistant.
27. A parenteral fluid warming system as claimed in claim 26, wherein said water resistant device defines a slot therein, said slot can be flushed out with water without damaging said water resistant device.
28. A fluid warming bag for use in a parenteral fluid warming system as a heat exchanger, said bag comprising an inlet and an outlet, and a counter flow fluid path extending between said inlet and said outlet in the same plane, said fluid path being a serpentine path having the coldest segment of said path located adjacent to the warmest segment of said path, said coldest segment being the segment of said fluid path receiving fluid from said inlet and said coldest segment being the segment of said fluid path providing fluid to said outlet, and said bag having alignment means in the form of parallel guide rails.

29. A fluid warming bag as claimed in claim 28 where said alignment means is provided for ensuring that said bag is registered within a fluid warmer device.

30. A fluid warming bag as claimed in claim 29 wherein said alignment means comprises at least two parallel guide rails of different size.

31. A fluid warming bag as claimed in claim 28 wherein said bag is made of four mil (0.004") three layer coextruded plastic.

32. A fluid warming bag as claimed in claim 29 wherein said alignment means comprises at least two parallel guide rails integrated into said fluid warming bag.

33. A fluid warming bag as claimed in claim 28 wherein said bag is made of polyethylene material.

34. A fluid warming bag as claimed in claim 28 wherein said bag is expandable plastic which can inflate to increase the surface area contact to enhance heat transfer.

35. A fluid warming bag for use in a parenteral fluid warming system as a heat exchanger, said bag comprising an inlet and an outlet, and a counter flow fluid path extending between said inlet and said outlet in the same plane, said fluid path being a serpentine path having the coldest segment of said path located adjacent to the warmest segment of said path, said coldest being the segment of said fluid path receiving fluid from said inlet and said warmest segment being the segment of said fluid path providing fluid to said outlet, and wherein an alignment means is provided for ensuring that said bag is registered within a fluid warmer device; and wherein said alignment means comprises at least two parallel guide rails of different color.

36. A parenteral fluid warming system comprising:
a) a fluid-warming bag having an inlet, and outlet, and a flow fluid path extending between said inlet and said outlet, said flow fluid path being a serpentine path, wherein the coldest fluid path portion is the portion of said fluid path receiving fluid from said inlet, and the warmest fluid path portion is the portion of said fluid path providing fluid to said outlet; and
b) a warmer device, having one energy reservoir with at least one heater, said bag being capable of being placed in thermal proximity to said energy reservoir such that said heater warms fluid passing through said fluid path; and
c) said fluid warming bag being provided with alignment means in the form of parallel guide rails and said warmer device being provided with cooperating registry means such that said bag, when inserted into said warmer device, precisely aligns and registers said fluid path.

37. The fluid warming bag as claimed in claim 36 wherein said alignment means are color coded.

38. The fluid warming bag as claimed in claim 36 wherein said flow fluid path is a counter flow fluid path.

39. A fluid warming bag for use in a parenteral fluid warming system as a heat exchanger, said bag comprising an inlet and an outlet, and a flow fluid path extending between said inlet and said outlet in the same plane, said fluid path being a serpentine path having the coldest segment being the segment of said fluid path receiving fluid from said inlet and the warmest segment being the segment of said fluid path providing fluid to said outlet, and wherein an alignment means in the form of parallel guide rails is provided for ensuring that said bag is registered within a fluid warmer device.

40. The fluid warming bag as claimed in claim 39 wherein said alignment means comprises at least two parallel guide rails.

41. The fluid warming bag as claimed in claim 40 wherein said parallel guide rails are of different color.

* * * * *

UNITED STATES PATENT AND TRADEMARK OFFICE
CERTIFICATE OF CORRECTION

PATENT NO. : 5,875,282
DATED : February 23, 1999
INVENTOR(S) : George Jordan and An Vu It is certified that error appears in the above-indentified patent and that said Letters Patent is hereby corrected as shown below:

Col. 9, line 13 - delete "evice" and insert -- device --

Col. 9, line 36 - delete "os" and insert -- of --

Signed and Sealed this

Fifth Day of October, 1999

Attest:

Q. TODD DICKINSON

Attesting Officer

Acting Commissioner of Patents and Trademarks